United States Patent
Saito et al.

(10) Patent No.: US 8,524,242 B2
(45) Date of Patent: Sep. 3, 2013

(54) SOLUBLE AGGREGATE, IMMUNE TOLERANCE INDUCER AND MANUFACTURING METHOD THEREOF

(75) Inventors: Akira Saito, Tsukuba (JP); Akio Kato, Yamaguchi (JP)

(73) Assignees: Wako Filter Technology Co., Ltd., Tokyo (JP); Protec Co., Ltd., Yamaguchi-shi (JP)

( * ) Notice: Subject to any disclaimer, the term of this patent is extended or adjusted under 35 U.S.C. 154(b) by 0 days.

(21) Appl. No.: 12/776,303

(22) Filed: May 7, 2010

(65) Prior Publication Data
US 2010/0330127 A1    Dec. 30, 2010

(30) Foreign Application Priority Data
Jun. 26, 2009    (JP) ................................. 2009-152712

(51) Int. Cl.
| A61K 39/00 | (2006.01) |
| A61K 39/35 | (2006.01) |
| A61K 39/36 | (2006.01) |
| A61K 39/38 | (2006.01) |
| C07K 1/00  | (2006.01) |
| C07K 14/00 | (2006.01) |
| C07K 17/00 | (2006.01) |

(52) U.S. Cl.
USPC ...................... 424/184.1; 424/275.1; 530/350

(58) Field of Classification Search
None
See application file for complete search history.

(56) References Cited

FOREIGN PATENT DOCUMENTS
| JP | 2002-249442 | 9/2002 |
| JP | 2005-034046 | 2/2005 |
| JP | 2005-104847 | 4/2005 |
| JP | 2006-340658 | 12/2006 |

OTHER PUBLICATIONS

Azakami et al. 'Role of Amyloid Type Cross-Structure in the Formation of Soluble Aggregate and Gel in Heat-Induced Ovalbumin.' J. Agric. Food Chem. 53:1254-1257, 2005.*
Sakaguchi et al. 'Epitope specificity ofIgE antibodies to a major allergen (Cry j 1) of Japanese cedar pollen in sera of humans and monkeys with pollinosis.' Immunology. 91:161-166, 1997.*
Kato et al. 'Estimation of the Molecular Weight Distribution of Heat-Induced Ovalbumin Aggregates by the Low-Angle Laser Light Scattering Technique Combined with High-Performance Gel Chromatography.' J. Agrlc. Food Chem. 35(5):633-637, 1987.*
Koppelman et al. 'Effect of Heat-Induced Aggregation on the IgE Binding of Patatin (Sol t 1) is Dominated by Other Potato Proteins.' J. Agric. Food Chem. 50:1562-1568, 2002.*
Walgraffe et al. 'A hypoallergenic variant of Der p 1 as a candidate for mite allergy vaccines.' J Allergy Clin Immunol. 123:1150-6, 2009.*
Laffer et al. 'Molecular characterization of recombinant T1, a non-allergenic periwinkle (*Catharanthus roseus*) protein, with sequence similarity to the Bet v 1 plant allergen family.' Biochem J. 373, 261-269, 2003.*
Bohle et al. 'Cooking birch pollen—related food: Divergent consequences for IgE- and T cell—mediated reactivity in vitro and in vivo.' J. Allergy. Clin. Immunol. 118:242-9, 2006.*
Koseki et al. 'Irreversible thermal denaturation and formation of linear aggregates of ovalbumin.' Food Hydrocolloids 3(2):123-134, 1989.*
Parker et al. 'The Use of Light-Scattering and Turbidity Measurements to Study the kinetics of Extensively Aggregating Proteins: alpha casein.' Biopolymers 16:2533-2547, 1977.*

* cited by examiner

*Primary Examiner* — Nora Rooney
(74) *Attorney, Agent, or Firm* — Alleman Hall McCoy Russell & Tuttle LLP

(57) ABSTRACT

A soluble aggregate of allergen proteins, prepared by heating multiple allergen proteins and aggregating the allergen proteins and thus enclosing the antigen structures causing allergic reactions therein.

2 Claims, 8 Drawing Sheets

SOLUBLE AGGREGATE, IMMUNE TOLERANCE INDUCER AND MANUFACTURING METHOD THEREOF

BACKGROUND OF THE INVENTION

1. Field of the Invention

The present invention relates to a soluble aggregate of allergen proteins having reduced antigenicity, an immunological tolerance-inducing agent containing the soluble aggregate and a production method thereof.

2. Description of the Background Art

Allergic diseases such as pollen allergy are diseases leading to generic or local disorders, which are caused by excessive reaction of the body's immune system to proteins generally called allergens (hereinafter, allergen proteins) that have invaded the body. In particular, 20% or more of Japanese people are suffering from Japanese cedar pollen allergy, causing a severe social problem.

These diseases are based on immune reactions inherent to human, and there is no established effective therapy. However, there are various possible therapies, including the method of eliminating allergen proteins and the symptomatic treatment with an anti-inflammatory agent described in JP-A No. 2005-34046, the method of reducing allergen proteins with a protein-denaturing agent described in JP-A No. 2005-104847, the desensitization therapy of suppressing allergic reactions by injecting a trace amount of allergen protein several times, as described in JP-A No. 2002-249442, and the like.

On the other hand, the present inventors earlier made an invention concerning a food composition that was prepared by modifying and coating the antigen structures of the allergen proteins therein with a polysaccharide by the Maillard reaction under dry conditions, from the viewpoint of allowing weakened allergen for oral administration, as described in JP-A No. 2006-340658.

SUMMARY OF THE INVENTION

An egg white protein ovalbumin is known to form a soluble aggregate via intermolecularly crosslinked β structures during thermal denaturation process. The ovalbumin is a glycoprotein having N-glycosidic bonds on Asn-292 and Asn-311. On the other hand, the major Japanese cedar pollen protein (Cry j 1) is a glycoprotein having N-glycosidic bonds on Asn-137, Asn-170, Asn-273 and Asn-333.

After intensive studies based on the similarity in structures between ovalbumin and the Japanese cedar pollen protein, Cry j 1, the present invention was made, based on the finding that the allergen proteins form a soluble aggregate, similarly to aggregation of ovalbumin, during thermal denaturation process, and the main object thereof is to reduce the antigenicity of allergen proteins.

Specifically, the soluble aggregate of allergen proteins according to the present invention is characterized by being prepared by heating multiple allergen proteins and aggregating the allergen proteins, and thus, enclosing the antigen structures causing allergic reactions (epitope) therein.

In other words, the soluble aggregate is formed, via β structures crosslinking denatured protein molecules (unfolded protein molecules) (cross-β-structures), similar to binding of amyloid-forming proteins. More specifically, when allergen proteins are heated, the β structure enclosed therein is exposed externally by thermal denaturation. Allergy-inducing epitopes are also exposed on the surface of the modified protein molecule then. And, the exposed β structures recombine with each other between the denatured proteins intermolecularly in the cooling process after heating. Then, the epitopes of allergen proteins are coated with the soluble aggregate formed by thermal denaturation. Thus, the epitopes of allergen proteins are enclosed in the soluble aggregate.

It is possible in this way to reduce the antigenicity of allergen proteins, without chemical modification of the antigen structure of allergen protein for example with polysaccharide. Thus by using the soluble aggregate, it is possible to induce immunological tolerance and prevent allergic diseases without anaphylaxis by introducing allergen proteins possibly causing allergic reaction into the immune system. Here, the "immunological tolerance" is a kind of immune reaction induced by uptaking of antigenic allergen proteins by M cells. It is known in the system that consistent oral or transmucosal administration of an antigen leads to production of suppressor T cells to the antigenic allergen proteins and mitigation of the immune reaction to the allergen protein.

The allergen in the present invention may be an animal or vegetable allergen, and in particular, the allergen may be a Japanese cedar pollen allergen.

When the allergen is a Japanese cedar pollen allergen, the allergen protein preferably aggregates, when heated at a programmed heating rate of 1° C./min from 40° C. to 90° C., for formation of the soluble aggregate without solidification of the Japanese cedar pollen allergen.

The immunological tolerance-inducing agent according to the present invention is also characterized in that it contains the soluble aggregate of allergen proteins described above and immunological tolerance is induced by oral or transmucosal administration thereof. The transmucosal administration would be, for example, sublingual desensitization therapy. Conventional sublingual desensitization therapies are those in which allergen proteins are administered into the immune system, as they are added dropwise onto the sublingual mucous membrane. Unintended intake of the allergen protein then may cause anaphylaxis for example on esophageal mucous membrane. On the other hand, the immunological tolerance-inducing agent according to the present invention, which is prepared by heating allergen proteins, forming the soluble aggregate and thus enclosing the antigen structure therein, can introduce the antigen structure into the immune system without contact with mucous membranes. Even when it is taken unintentionally, it can be incorporated by the intestinal immune system without the risk of anaphylaxis.

The method of producing an immunological tolerance-inducing agent according to the present invention is a method of producing an immunological tolerance-inducing agent inducing immunological tolerance by oral or transmucosal administration, characterized by heating multiple allergen proteins, aggregating the allergen proteins and thus enclosing the allergic reaction-causing antigen structures therein.

The present invention in such a configuration can reduce the antigenicity of allergen proteins and provide an unprecedented completely new immunological tolerance-inducing agent.

BRIEF DESCRIPTION OF THE DRAWINGS

FIG. 1 is a chart of photographs showing, by shading, the binding to an IgE antibody after dot blotting;

FIG. 2 is a graph showing the binding degree to the IgE antibody;

FIG. 3 is a chart showing the gel filtration patterns of unheated Cryj1 and the soluble aggregate by HPLC;

FIG. 4 is a chart showing the SDS-PAGE pattern of unheated Cry j 1 and the soluble aggregate;

DESCRIPTION OF THE PREFERRED EMBODIMENTS

Figure 1:
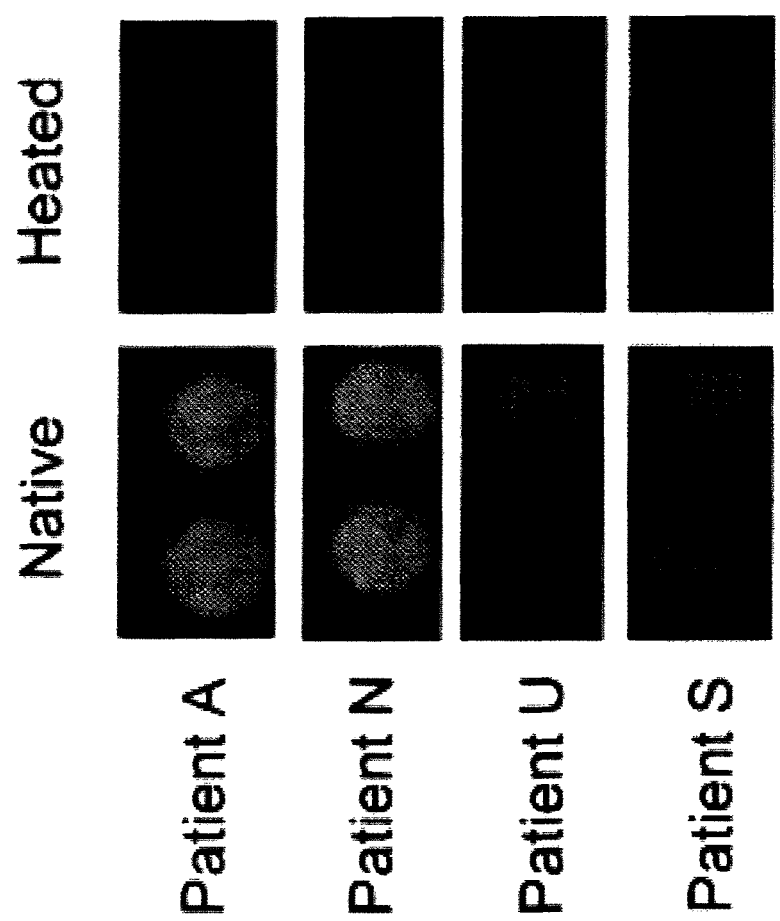

Hereinafter, the immunological tolerance-inducing agent according to the present invention will be described together with its production method.

The immunological tolerance-inducing agent in the present embodiment is an immunological tolerance-inducing agent inducing immunological tolerance to Japanese cedar pollen allergens by oral or transmucosal administration, for example in sublingual desensitization therapy, which is produced by heating multiple pieces of Japanese cedar pollen allergen (Cry j 1) and thus aggregating the allergen Cry j 1 and thus enclosing the antigen structures causing allergic reactions therein.

The allergen Cry j 1, when heated, forms intermolecularly crosslinked β structures that are connected to each other intermolecularly through disulfide bonds. The antigen structures exposed on the molecular surface (IgE epitopes) are then enclosed in the soluble aggregate, and the antigenicity of Cry j 1 is reduced.

The immunological tolerance-inducing agent is produced by the following procedure:

<Purification of Cry j 1>

100 g of Japanese cedar pollen was added to 2 L of 0.1 M phosphate buffer solution (pH 8.0, containing NaCl (0.14 M) and KCl (0.01 M)), and the mixture was stirred gently for 1 hour. Then, the supernatant was separated by centrifugation (15,000×g, 30 min) or filtration with flocculant. Ammonium sulfate was added to the supernatant to 80% saturation (561 g/L); the mixture was stirred at 4° C. overnight; and the resulting precipitate was collected by centrifugation (18,500×g, 40 min). The precipitate was dissolved in distilled water and the solution was dialyzed. The dialysate thus processed was freeze-dried and stored as a crude extract of Cry j 1 (hereinafter, referred to as CE).

The CE was dissolved in 0.01 M acetate buffer solution (pH 5.0) which was subjected to cation-exchange chromatographic column (CM-Toyopearl, manufactured by Tosoh Co., Ltd.) previously equilibrated with 0.01 M acetate buffer solution (pH 5.0). The column was then washed with 0.01 M acetate buffer solution (pH 5.0) and the adsorbed proteins were eluted with NaCl gradient (in 0.01 M acetate buffer solution) from 0.05 M to 0.3 M. The protein corresponding to the peak of absorbance at 280 nm was collected, dialyzed against distilled water and freeze-dried.

<Preparation of Soluble Aggregate>

10 mM acetate buffer solution (pH 5.0) containing Cry j 1 dissolved to an amount of 0.1% was heated at a programmed heating rate of 1° C./min from 40° C. to 90° C. It was possible to obtain a transparent soluble aggregate without solidification under such a controlled condition. The soluble aggregate was used in the following tests, after being cooled at room temperature. The soluble aggregate thus obtained can be stored without deterioration in properties, for example, as dissolved in glycerol solution for example at a concentration of 20% or more and the solution is stored at low temperature, for example, at minus 25° C.

EXAMPLES

Binding between a thermally denatured Cry j 1 soluble aggregate and IgE was analyzed. The anti-sera of Japanese cedar pollen patients used were provided from the Dermatology Dept., Yamaguchi University Hospital (Dr. M. Muto).

Binding between Cry j 1 after heating (hereinafter, referred to as "heated Cry j 1") and the IgE antibody of patient was analyzed by using the "dot blot" method. The dot blotting was carried out by using the biotin-avidin method. Native Cry j 1 (hereinafter, referred to as "unheated Cry j 1") and the Cry j 1 heated at a programmed heating rate of 1° C./min from 40° C. to 90° C. were diluted to 0.0005%, and 10 μL of each diluted solution of unheated or heated Cry j 1 was applied dropwise on a PVDF (polyvinylidene fluoride) membrane. The PVDF membrane was previously cleaned by using methanol. IgE bound to Cry j 1 was detected by using the biotin-avidin reaction. After drying, the PVDF membrane was incubated with a blocking agent (0.5% BSA in PBS-Tween) for 1 hour and washed three times with PBS-Tween for removal of unneeded BSA. The PVDF membrane was cultured overnight together with patient's serum diluted 20 times with PBS-Tween. The PVDF membrane was washed four times with PBS-Tween; a biotinylated anti-human IgE antibody diluted to 1/10000 was then applied to the PVDF membrane; and the mixture was cultured for 1 hour. The membrane was then washed four times with PBS-Tween, and the IgE antibody bound was detected by Western blotting by using HRP-streptavidin solution diluted to 1/5000 and ECL Plus (GE Healthcare).

Figure 2:
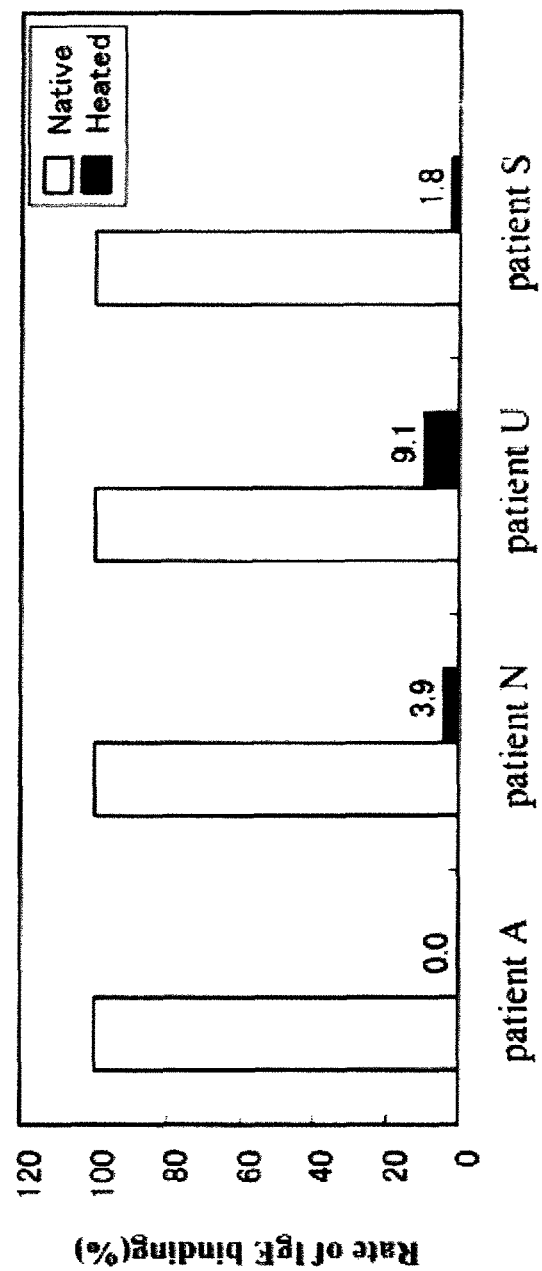

FIG. 1 is a chart of photographs showing the binding to the IgE antibody after dot blotting by shading, wherein whiter color indicates stronger binding to the IgE antibody. In FIG. 1, the term "Native" represents the unheated Cry j 1, while the term "Heated" represents the heated Cry j 1. Alternatively, FIG. 2 is a graph showing the results obtained by measuring the shading shown in FIG. 1 with a densitometer and it is thus a graph showing the binding degree to the IgE antibody. The binding degree between the heated Cry j 1 and the IgE antibody is a relative value, compared to 100% of the binding between the unheated Cry j 1 and the IgE antibody.

As obvious from these FIGS. 1 and 2, the binding degree of the heated Cry j 1 to the IgE antibody is distinctively lower than that of unheated Cry j 1. In other words, Cry j 1, when heated, forms intermolecularly crosslinked β structures that are connected to each other via intermolecular disulfide bonds, wherein the antigen structure exposed on the molecular surface is enclosed in the soluble aggregate, and thus has decreased antigenicity.

Finally, results obtained by analysis of the soluble aggregate in the present embodiment by liquid chromatography (HPLC), sodium dodecylsulfate-polyacrylamide gel electrophoresis (SDS-PAGE), circular dichroism (CD) analysis and fluorescence analysis will be described.

Figure 3:
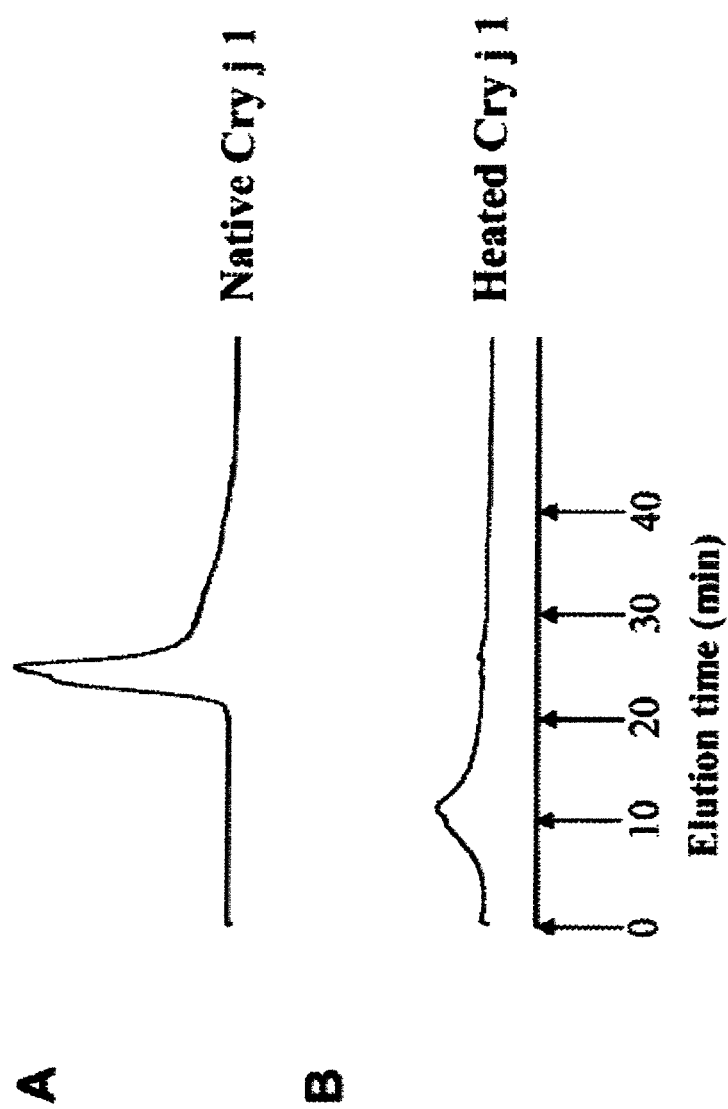

FIG. 3 is a chart showing the gel filtration patterns obtained when the unheated Cry j 1 and the heated Cry j 1 are analyzed by HPLC. In FIG. 3, the abscissa shows the elution period, and A indicates the pattern of the unheated Cry j 1, while B indicates the pattern of the heated Cry j 1. The analysis was made by HPLC, by using TSK gel G-3000 SW (manufactured by Tosoh Corporation, column size: 0.75×30 cm). 100 mM of the unheated or heated Cry j 1 was fed into the HPLC column at a flow rate 0.5 mL/min, by using sodium phosphate buffer solution (pH 7.0). The gel filtration pattern was monitored by using absorbance at a wavelength of 280 nm.

As obvious from FIG. 3, the peak of the unheated Cry j 1 emerges as a bimodal peak consisting of two peaks having elution times of 24.5 min and 25 min. Alternatively, the peak of the heated Cry j 1 does not emerge as peaks having elution times of 24.5 min and 25 min, indicating formation of the soluble aggregate.

Figure 4:
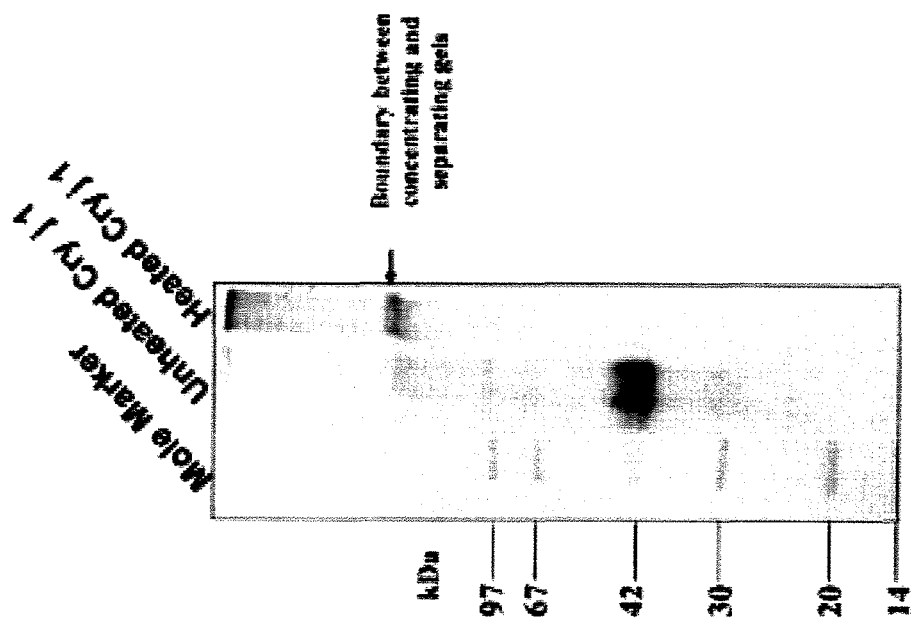
Figure 5:
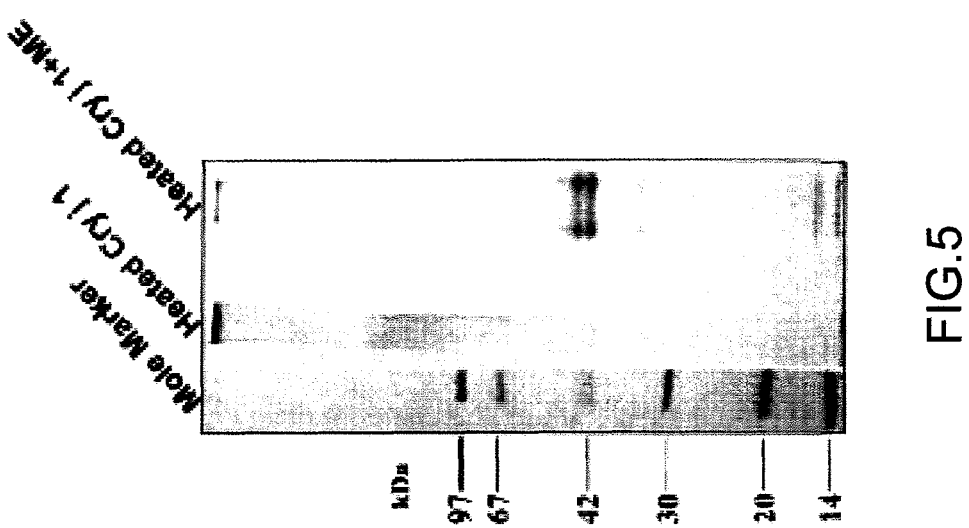
FIG. 5 is a chart showing the SDS-PAGE pattern of the soluble aggregate and the soluble aggregate in the presence of 2-mercaptoethanol.

FIGS. 4 and 5 show results obtained by SDS-PAGE analysis of the unheated Cry j 1 and the heated Cry j 1 and also of Cry j 1 heated in the presence of 2-mercaptoethanol. In FIG. 4, the left lane shows molecular weight markers; the middle lane shows the SDS-PAGE pattern of the unheated Cry j 1; and the right lane, those of the heated Cry j 1. Alternatively in FIG. 5, the left lane shows molecular weight markers; the middle lane, the SDS-PAGE results of the heated Cry j 1; and the right lane, those of the heated Cry j 1 in the presence of 2-mercaptoethanol. A 12.5% acrylamide separation gel containing 0.1% SDS and a 5% acrylamide concentration gel were used in the SDS-PAGE analysis. Electrophoresis was carried out, while a current of 10 mA was applied to the concentration gel in the electrophoretic buffer solution (tris-glycine (pH 8.0)) containing 1% SDS for 30 minutes and a current of 20 mA to the separation gel for 1 hour. After the electrophoresis, the gel sheet was stained with a protein-staining dye (0.2% Coomassie Brilliant Blue R-250 (CBB-R250)) and bleached with 10% acetic acid containing 20% methanol.

As obvious from FIG. 4, the molecular weight of the unheated Cry j 1 is shown to be 42 to 45 kDa, as it reflects the N-glycosidic bond of the protein. Alternatively, the heated Cryj1 appears at the area close to the boundary between separating and concentration gels, indicating formation of the soluble aggregate. Further as obvious from FIG. 5, the heated Cry j 1 heated in the presence of 2-mercaptoethanol is separated by the separating action of 2-mercaptoethanol, indicating that it has a molecular weight similar to that of unheated Cry j 1. Thus, it was found that intermolecular disulfide bond formation is involved in polymerization of Cry j 1 by heating.

Figure 6:
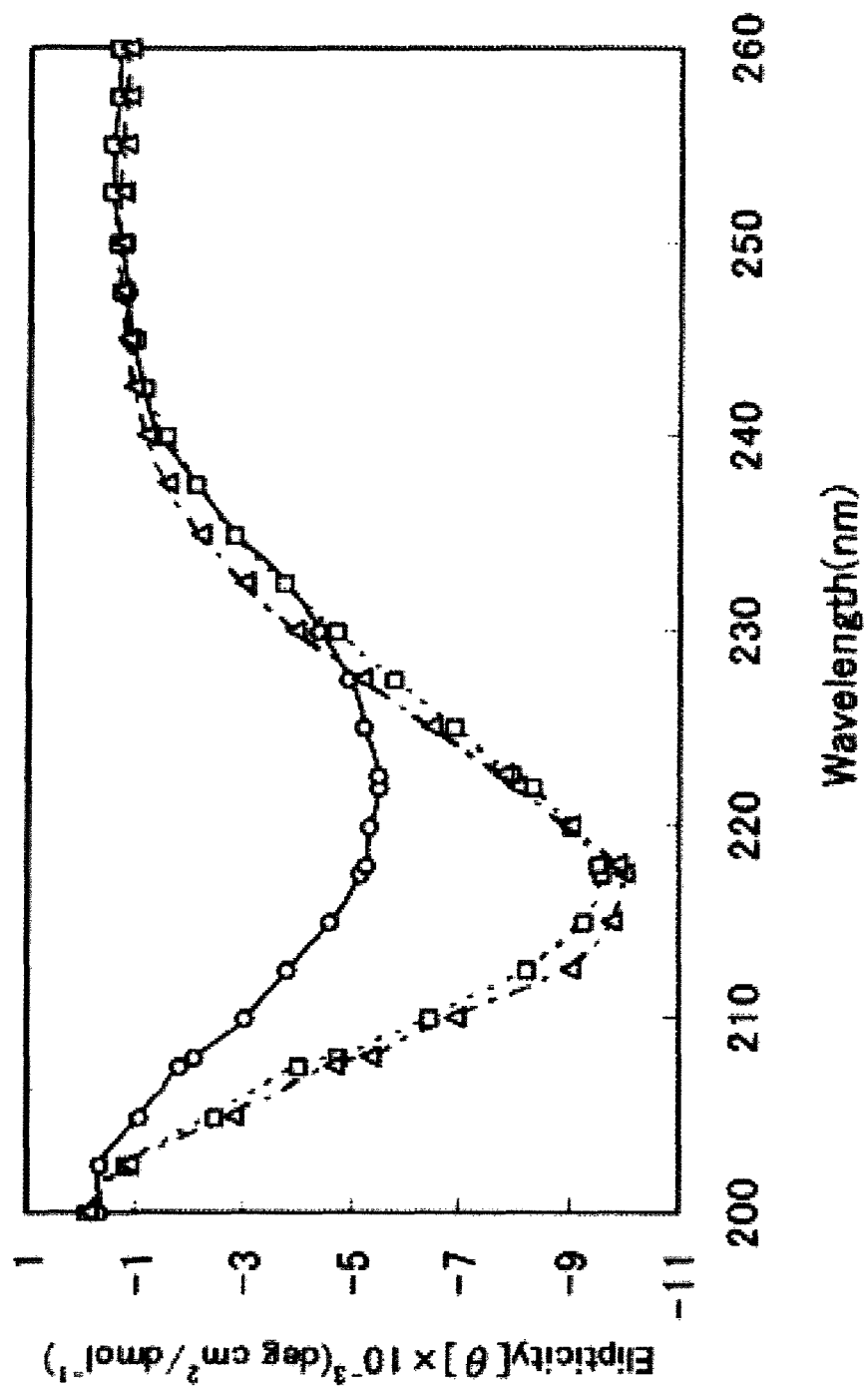
FIG. 6 is a graph showing the CD spectra of Cry j 1 before, during and after heating.

FIG. 6 shows the CD spectra of Cry j 1 before, during and after heating. In FIG. 6, "○-○" indicates the spectrum of Cry j 1 at room temperature; "□-□" indicates the spectrum of Cry j 1 heated to 90° C.; and "Δ-Δ" indicates the spectrum of Cry j 1 after cooling from the heated state. The CD-measuring instrument used was a spectropolarimeter (manufactured by JASCO, Model J-600) using the ellipticity at a measurement wavelength of 200 to 260 nm at 25° C. The final concentration of Cryj1 in the 10 mM acetate buffer solution (pH 5.0) placed in a cell having a light path of 1.0 mm was set to 1 mg/mL. Each sample was analyzed by two to four continuous scans and the average value was calculated. Each spectrum was normalized by protein concentration, to give a mean residue molar ellipticity (deg cm$^2$/d mol). The protein concentration was calculated from the absorbance at 280 nm. The thermal denaturation curve was determined automatically at an ellipticity of 222 nm in the range of 40 to 90° C.

As obvious from FIG. 6, the heated Cry j 1 shows a characteristic CD curve different from that of conventional protein. Most CD spectra of proteins normally show a peak, which is generated in a thermal denaturation process, in the wavelength region smaller than 210 nm. However, the CD spectrum of the thermally denatured Cry j 1 shows absorption minimal at a wavelength of 218 nm, indicating that the amount of β structure was increased by thermal denaturation.

It was also found that the trend became more distinctive when solution of thermally denatured Cry j 1 was cooled and the amount of the β structure was increased when the thermally denatured Cry j 1 was cooled. Such results reflect the increase in the amount of intermolecular β sheet structure.

Figure 7:
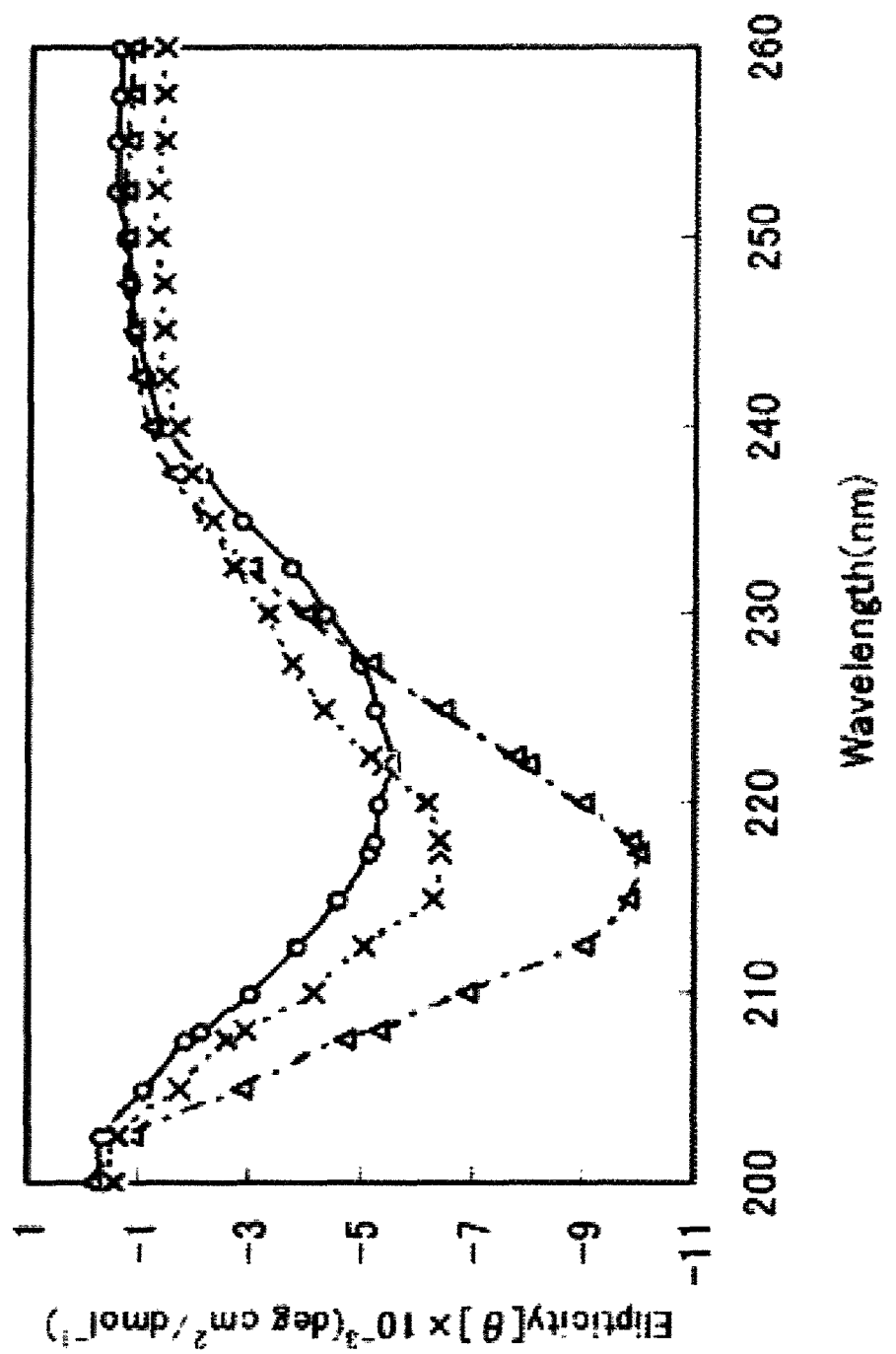
FIG. 7 is a graph showing the CD spectra of Cry j 1 heated at 90° C. and Cry j 1 treated with guanidine hydrochloride after heating.

Alternatively, FIG. 7 is a chart showing the CD spectra of the unheated Cry j 1, Cry j 1 heated at 90° C. and Cry j 1 treated with a modifying agent (4 M guanidine hydrochloride) after heating. In FIG. 7, "○-○" indicates a spectrum of the unheated Cry j 1; "Δ-Δ" indicates the spectrum of the Cry j 1 heated at 90° C.; and "x-x" indicates the spectrum when a modifying agent was added to the Cry j 1 after heating. As obvious from this Figure, the absorbance of the thermally denatured Cry j 1 at the wavelength of 218 nm decreased significantly, when a modifying agent was added, indicating that the intermolecularly crosslinked β structure was destroyed by addition thereof. These results demonstrate that Cry j 1, by thermal denaturation, forms a soluble aggregate having an ordered integrated structure via intermolecular β structures.

Figure 8:
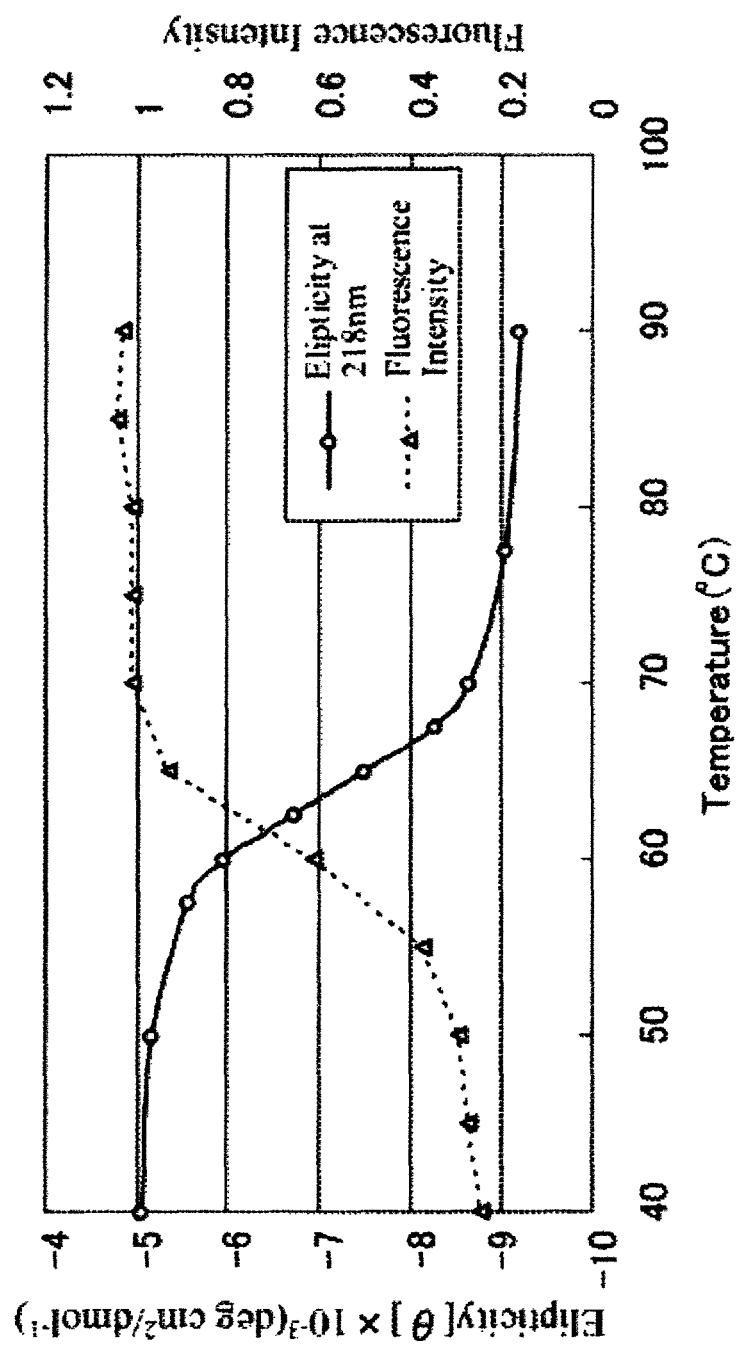
FIG. 8 is a graph showing a thermal denaturation curve obtained by CD at 218 nm and the fluorescence intensity of thioflavin T during a thermal denaturation process of Cry j 1.

For analysis of the intermolecular β structures formed by the soluble aggregate, fluorescence intensity analysis by using thioflavin T was performed. Thioflavin T is known to have a reaction to β structures, and it is also known that the fluorescence intensity of the thioflavin T is in parallel with the β structure. FIG. 8 is a chart showing a thermal denaturation curve by CD at 218 nm and the fluorescence intensity of the thioflavin T in the thermal denaturation process of Cryj1. In FIG. 8, "○" indicates an ellipticity at a wavelength of 218 nm, and "Δ" indicates a fluorescence intensity.

As is obvious from FIG. 8, the fluorescence intensity of the thioflavin T in the Cry j 1 increases, as the heating temperature is raised. The results demonstrate that Cry j 1 forms the β-structure by intermolecular interaction in a thermal denaturation process. In other words, intermolecular disulfide bonds and intermolecular cross β structure are involved in the polymerization of Cry j 1 caused by heating.

SUMMARY

Advantageous Effects of the Present Embodiment

The immunological tolerance-inducing agent in the present embodiment in the configuration above can decrease the antigenicity of an allergen protein without chemical modification of the antigen structure of the allergen protein for example with polysaccharide. It is thus possible, by means of using the immunological tolerance-inducing agent, to induce immunological tolerance and prevent allergic diseases by introducing an allergen protein that may cause allergic reaction into the immune system by oral or transmucosal administration without anaphylaxis.

Other Modified Embodiment

The present invention is not limited to the embodiment above.

For example in the above embodiments, an immunological tolerance-inducing agent to Japanese cedar pollen allergen was described, but the agent is applicable to other vegetable and animal antigens such as Japanese cypress pollen allergen.

In addition, it is needless to say that the present invention is not limited to the above embodiments and various modifications are possible within the scope of the invention.

What is claimed is:

1. A method of producing a soluble aggregate of Cry j 1 cedar pollen allergen proteins, comprising:

heating multiple Cry j 1 cedar pollen allergen proteins, which are dissolved in an acetate buffer solution, at a heating rate of 1° C./min from 40 to 90° C., to thereby aggregate these Cry j 1 cedar pollen allergen proteins and to thus enclose antigen structures causing allergic reactions therein, to obtain a transparent and soluble aggregate without solidification.

2. A method of producing an immunological tolerance-inducing agent inducing immunological tolerance by oral or transmucosal administration, comprising:

heating multiple Cry j 1 cedar pollen allergen proteins, which are dissolved in an acetate buffer solution, at a heating rate of 1° C./min from 40 to 90° C., to thereby aggregate these Cry j 1 cedar pollen allergen proteins and to thus enclose antigen structures causing allergic reactions therein, to obtain a transparent soluble aggregate without solidification.

* * * * *